United States Patent
Singh et al.

(10) Patent No.: US 12,115,162 B2
(45) Date of Patent: Oct. 15, 2024

(54) PALATABLE FORMULATIONS

(71) Applicant: Zoetis Services LLC, Parsippany, NJ (US)

(72) Inventors: Paramjit Singh, Navi Mumbai (IN); Debendra Kumar Panda, Navi Mumbai (IN); Jeffrey Ellis Price, Middlebury, IN (US); Atul Chhagan Badhan, Navi Mumbai (IN); Nicholas Finn Cunningham, Kalamazoo, MI (US)

(73) Assignee: Zoetis Services LLC, Parsippany, NJ (US)

(*) Notice: Subject to any disclaimer, the term of this patent is extended or adjusted under 35 U.S.C. 154(b) by 588 days.

(21) Appl. No.: 17/421,533

(22) PCT Filed: Feb. 19, 2020

(86) PCT No.: PCT/US2020/018762
§ 371 (c)(1),
(2) Date: Jul. 8, 2021

(87) PCT Pub. No.: WO2020/172232
PCT Pub. Date: Aug. 27, 2020

(65) Prior Publication Data
US 2022/0062287 A1 Mar. 3, 2022

Related U.S. Application Data

(60) Provisional application No. 62/807,871, filed on Feb. 20, 2019.

(51) Int. Cl.
*A61K 31/519* (2006.01)
*A61K 9/00* (2006.01)
*A61K 47/46* (2006.01)

(52) U.S. Cl.
CPC .......... *A61K 31/519* (2013.01); *A61K 9/0056* (2013.01); *A61K 47/46* (2013.01)

(58) Field of Classification Search
CPC ..... A61K 31/519; A61K 9/0056; A61K 47/46
See application file for complete search history.

(56) References Cited

U.S. PATENT DOCUMENTS

| | | |
|---|---|---|
| 2004/0037869 A1 | 2/2004 | Cleverly et al. |
| 2005/0165091 A1 | 7/2005 | Li et al. |
| 2006/0141009 A1 | 6/2006 | Huron et al. |
| 2006/0222684 A1 | 10/2006 | Isele |
| 2007/0128251 A1 | 6/2007 | Paulsen et al. |
| 2008/0075759 A1* | 3/2008 | Paulsen ............ A61P 25/04 424/439 |
| 2008/0160067 A1 | 7/2008 | Boeckh et al. |
| 2008/0280274 A1 | 11/2008 | Friesen et al. |
| 2010/0075996 A1 | 3/2010 | Mitton-Fry et al. |
| 2014/0141055 A1 | 5/2014 | Kluger et al. |
| 2014/0343004 A1* | 11/2014 | Derrieu ............ A23K 40/25 514/30 |
| 2015/0150820 A1 | 6/2015 | Laczay |
| 2016/0158147 A1 | 6/2016 | Singer |
| 2017/0354593 A1 | 12/2017 | Majumdar et al. |
| 2018/0169008 A1 | 6/2018 | Dixit et al. |

FOREIGN PATENT DOCUMENTS

| | | |
|---|---|---|
| EP | 0 320 320 A2 | 12/1992 |
| FR | 0320320 B1 * | 6/1989 |

OTHER PUBLICATIONS

Apoquel Oclacitinib Tablet, May 14, 2013 https://animaldrugsatfda.fda.gov/adafda/views/#/home/previewsearch/141-345 (Year: 2013).*
Ashika Advankar at al., Chapter 13—Specialized tablets: ancient history to modern developments, Editor(s): Rakesh K. Tekade, In Advances in Pharmaceutical Product Development and Research, Drug Delivery Systems, Academic Press, 2019, pp. 615-664 (Year: 2019).*
Rong-Kun Chang, Michael Leonzio, Munir A. Hussain & M. A. Hussain (1999) Effect of Colloidal Silicon Dioxide on Flowing and Tableting Properties of an Experimental, Crosslinked Polyalkylammonium Polymer, Pharmaceutical Development and Technology, 4:2, 285-289, (Year: 1999).*
Daoudal (EP0320320B1) English machine translation (machine translated Mar. 25, 2024) (Year: 2024).*
Avinash G. Thombre, Advanced Drug Delivery Reviews 56 (2004) 1399-1413. (Year: 2004).*
Apoquel Oclacitinib Tablet, May 14, 2013 https://animaldrugsatfda.fda.gov/adafda/views/#/home/previewsearch/141-345 (Year: 2013) (Year: 2013).*
Ashika Advankar at al., Chapter 13—Specialized tablets: ancient history to modern developments, Editor(s): Rakesh K. Tekade, In Advances in Pharmaceutical Product Development and Research, Drug Delivery Systems, Academic Press, 2019, pp. 615-664 (Year: 2019) (Year: 2019).*
Daoudal (EP0320320B1) English machine translation (machine translated Mar. 25, 2024) (Year: 2024) (Year: 2024).*
Avinash G. Thombre, Advanced Drug Delivery Reviews 56 (2004) 1399-1413. (Year: 2004) (Year: 2004).*

(Continued)

*Primary Examiner* — Clinton A Brooks
*Assistant Examiner* — Izabela Schmidt
(74) *Attorney, Agent, or Firm* — Paul M. Misiak

(57) ABSTRACT

The present invention is directed to a soft chewable composition comprising or containing a therapeutically effective amount of a veterinary active agent, preferably a JAK inhibitor; an animal based palatant, a non-animal based palatant, a flavor modifier, and at least one veterinary acceptable excipient that is selected from at least one each of a disintegrant, binder, lubricant, humectant, and glidant; and wherein the soft chewable tablet is compressed with a rotary tablet press; and methods for treating or preventing cancer, asthma, atopic dermatitis, autoimmune disorders, pruritus associated with allergic dermatitis, allergies, and chronic respiratory disease in an animal.

15 Claims, No Drawings

(56) References Cited

OTHER PUBLICATIONS

Rong-Kun Chang, Michael Leonzio, Munir A. Hussain & M. A. Hussain (1999) Effect of Colloidal Silicon Dioxide on Flowing and Tableting Properties of an Experimental, Crosslinked Polyalkylammonium Polymer, Pharmaceutical Development and Technology, 4:2, 285-289, (Year: 1999) (Year: 1999).*

Fleck T., et al., "FC-36 Comparison of the janus kinase (JAK) inhibitor, oclacitinib, and prednisolone in canine models of pruritus," Veterinary Dermatology: "Plenary Session Abstracts: Thursday Morning, Jul. 26 Theme: Allergy," Veterinary Dermatology, vol. 23 (Suppl. 1), pp. 2-104, Jan. 1, 2012 (*p. 38).

\* cited by examiner

PALATABLE FORMULATIONS

CROSS-REFERENCE TO RELATED APPLICATIONS

This application is a US National Stage entry of International Application No. PCT/US2020/018762, filed Feb. 19, 2020, which claims the benefit of U.S. Provisional Application No. 62/807,871, filed Feb. 20, 2019.

FIELD OF INVENTION

This invention describes a stable, palatable soft chewable composition that comprises at least one veterinary acceptable active ingredient, at least one animal based palatant, at least one non-animal based palatant, and at least one additional veterinary acceptable excipient; and methods of use for treating and/or preventing many diseases, including but not limited to cancer, cardiovascular diseases, allergies, asthma and other respiratory diseases, autoimmune diseases, inflammatory diseases, bone diseases, and other metabolic disorders. The soft chew tablets are prepared without extrusion and are compressed with a rotary tablet press.

BACKGROUND OF THE INVENTION

Protein kinases are families of enzymes that catalyze the phosphorylation of specific residues in proteins, broadly classified into tyrosine and serine/threonine kinases. Inappropriate kinase activity, arising from mutation, over-expression, or inappropriate regulation, dis-regulation or de-regulation, as well as over- or under-production of growth factors or cytokines has been implicated in many diseases, including but not limited to cancer, allergies, asthma and other respiratory diseases, autoimmune diseases, and inflammatory diseases. Inappropriate kinase activity triggers a variety of biological cellular responses relating to cell growth, cell differentiation, survival, apoptosis, mitogenesis, cell cycle control, and cell mobility.

Thus, protein kinases have emerged as an important class of enzymes as targets for therapeutic intervention. In particular, the JAK family of cellular protein tyrosine kinases (JAK-1, JAK-2, JAK-3, and Tyk-2) play a central role in cytokine signaling (Kisseleva et al, Gene, 2002, 285, 1; Yamaoka et al. Genome Biology 2004, 5, 253)). Upon binding to their receptors, cytokines activate JAK which then phosphorylate the cytokine receptor, thereby creating docking sites for signaling molecules, notably, members of the signal transducer and activator of transcription (STAT) family that ultimately lead to gene expression. Numerous cytokines are known to activate the JAK family.

Formulation of a drug (i.e., active agent) into an edible medication, such as a palatable, chewable dosage form, can increase subject acceptance of the medication, especially animals that tend to resist swallowing tablets or capsules and chewing bitter and/or granular dosage forms. Flavorings and polymeric coatings have commonly been used to provide some degree of palatability to the dosage form. Chewable compositions can be prepared by granulating the active veterinary ingredient with oils, fats, waxes, and water to prepare a dough-like composition for extrusion processes. These compositions, however, tend to be oily and gummy. Other chewable compositions can be prepared in a similar manner, but the dough is rolled into a sheet of different thicknesses and then punch-cut into appropriate sizes. The present invention achieves a palatable soft chew composition that can be compressed into tablets via rotary compression.

Soft chews have been described previously. However, the prior palatable tablets have been prepared using non-animal based palatants (WO2004/016252), use of partially pre-gelatinized starch (WO2005/013714); formulations with 5-30% weight of fats, waxes, and oils (WO2014/033230) which tend to impart a "greasy" feel to the tablet; blending API (with or without oil) with dry excipients under low-shear conditions and wherein each process step is conducted without the introduction of heat (WO2007/067582) for heat labile actives; formation of dough like compositions for compression with a rotary molding machine (WO2014/079825); use of sugar (5-75%) as a sweet filler (WO2004/014143); and manufacture of a soft (<2 kp) tablet comprising 5-20% oil and 5-20% glycerol (WO2017/106812). The composition of the invention does not incorporate fats, oils, pre-gelatinized starches, sugar(s), and the like; but rather prepares a common blended and milled granulate that can be easily compressed into tablets using a rotary tablet press.

SUMMARY OF THE INVENTION

In accordance with this invention, it has been discovered that the oral compositions of the invention are stable, palatable, safe, and efficacious. Increased stability correlates with increased shelf-life, and optimally, efficacy, while palatability increases patient compliance. In addition, the granulation can be compressed with a rotary tablet press.

In one aspect, the invention describes soft chew veterinary compositions comprising or containing a veterinary active ingredient; at least one animal based palatant, at least one non-animal based palatant; and at least one veterinary acceptable excipient. In another aspect, the at least one veterinary acceptable excipient includes at least one of each of a disintegrant, binder, humectant, glidant, and lubricant; and wherein the composition is compressed with a rotary tablet press.

In one aspect, the invention describes soft chew veterinary compositions comprising or containing a veterinary active ingredient, wherein said active ingredient is a JAK inhibitor, at least one animal based palatant, at least one non-animal based palatant, and at least one veterinary acceptable excipient comprising at least one of each of a disintegrant, binder, humectant, glidant, and lubricant; and wherein the composition is compressed with a rotary tablet press.

In one aspect, the invention describes soft chew veterinary compositions comprising or containing a veterinary active ingredient, wherein said active ingredient is the JAK inhibitor, oclacitinib, N-methyl-1-{trans-4-[methyl(7H-pyrrolo[2,3-d]pyrimidin-4-yl)amino]cyclohexyl}-methanesulfonamide, or a veterinary acceptable salt thereof; at least one animal based palatant, at least one non-animal based palatant, and at least one veterinary acceptable excipient. In another aspect, the active ingredient is oclacitinib maleate (Apoquel®; N-methyl-1-{trans-4-[methyl(7H-pyrrolo[2,3-d]pyrimidin-4-yl)amino]cyclohexyl}-methanesulfonamide (2Z)-2-butenedioate (maleate)) and the composition comprises at least one animal based palatant, at least one non-animal based palatant, and at least one veterinary acceptable excipient selected from at least one of each of a disintegrant, binder, humectant, glidant, and lubricant. In one aspect, the amount of oclacitinib maleate is in the amount of about 4 w/w % to 5 w/w % of the total weight of the tablet. In one aspect, the amount of oclacitinib maleate is in the amount of about 4 w/w % (4.03 w/w %) of the total weight of the tablet.

In another aspect of the invention, the composition comprises or contains at least two palatants in the amount of about 55 w/w % to about 70 w/w %, including one animal based palatant and one non-animal based palatant. In another aspect of the invention, the animal based palatant is in the amount of about 45 w/w % to about 55 w/w % of the total tablet weight. In another aspect, the animal based palatant is in the amount of about 46 w/w % to about 52 w/w % of the total weight of the tablet. The preferred amount of the animal-based palatant is about 48 w/w % to about 50 w/w % of the total weight of the tablet. The preferred animal based palatant is derived from swine (pig). The more preferred animal based palatant is derived from pig liver. The most preferred animal based palatant is pork liver powder. In another aspect of the invention, the non-animal based palatant is in the amount of about 10 w/w % to about 15 w/w % of the total weight of the tablet. In another aspect, the preferred amount of the non-animal based palatant is in the amount of about 11 w/w % to about 14 w/w % of the total weight of the tablet. The preferred non-animal based palatant is yeast. The preferred yeast is Brewer's yeast. In another aspect of the invention, the composition comprises about 46 w/w % to about 52 w/w % of an animal based palatant and about 11 w/w % to about 14 w/w % of a non-animal based palatant, both accounting for the w/w % of the total weight of the tablet.

In another aspect of the invention, the composition comprises or contains about 0.4 w/w % to about 0.6 w/w % of the total weight of the tablet of a flavor modifier. The preferred flavor modifier is sodium chloride or potassium chloride. The preferred flavor modifier is sodium chloride.

In another aspect of the invention, the composition further comprises or contains at least one veterinary acceptable excipient selected from at least one each of a disintegrant, binder, humectant, lubricant, and glidant.

In one aspect of the invention, the at least one disintegrant is in the amount of about 8 w/w % to about 18 w/w % of the total weight of the tablet. In yet another aspect, the at least one disintegrant is in the amount of about 10 w/w % to about 15 w/w % of the total weight of the tablet. In one aspect, the disintegrant is selected from the group consisting of crospovidone, sodium starch glycolate, or mixture thereof. In another aspect, the disintegrant is a mixture of magnesium stearate and glyceryl monostearate.

In yet another aspect of the invention, the at least one binder is in the amount of about 5 w/w % to about 7 w/w % of the total weight of the tablet. In another aspect, the binder is in the amount of about 5 w/w % to about 6.5 w/w % of the total weight of the tablet. In one aspect, the at least one binder is selected from the group consisting of polyethylene glycol, a gum, or mixture thereof. The preferred polyethylene glycol is polyethylene glycol 3350; and the preferred gum is xanthan gum. In one aspect, the composition comprises or contains a mixture of polyethylene glycol 3350 and xanthan gum. In one aspect, the amount of polyethylene glycol 3350 is in the amount of about 5 w/w % to about 6 w/w % of the total weight of the tablet.

In another aspect of the invention, the at least one humectant is in the amount of about 10 w/w % to about 15 w/w % of the total weight of the tablet. In another aspect, the humectant is in the amount of about 11 w/w % to about 14 w/w % of the total weight of the tablet. In one aspect, the humectant is glycerol.

In another aspect of the invention, the at least one lubricant is about 1 w/w % to about 2 w/w % of the total weight of the tablet. In another aspect, the lubricant is selected from the group consisting of magnesium stearate, glycerol monostearate, or mixture thereof. In another aspect, the lubricant is a mixture of magnesium stearate and glyceryl monostearate.

In another aspect of the invention, the at least one glidant is in the amount of about 1 w/w % to about 3 w/w % of the total weight of the tablet. The preferred amount of glidant is about 1.5 w/w % to about 2.5 w/w % of the total weight of the tablet. In one aspect, the glidant is colloidal silicon dioxide.

In yet another aspect of the invention, is a palatable soft chewable tablet veterinary composition comprising or containing a therapeutically effective amount of oclacitinib maleate in the amount of about 4 w/w % to about 5 w/w %; an animal based palatant in the amount of about 46 w/w % to about 52 w/w %; a non-animal based palatant in the amount of about 11 w/w % to about 14 w/w %; a flavor modifier in the amount of about 0.4 w/w % to about 0.6 w/w %; at least one disintegrant in the amount of about 10 w/w % to about 15 w/w %; at least one binder in the amount of about 5 w/w % to about 7 w/w %; at least one humectant in the amount of 11 w/w % to about 14 w/w %, at least one glidant in the amount of about 1 w/w % to about 3 w/w %, and at least one lubricant in the amount of about 1 w/w % to about 2 w/w %; and wherein each of the w/w % are based on the total weight of the tablet. In yet another aspect of the invention, is a palatable soft chewable tablet veterinary composition containing a therapeutically effective amount of oclacitinib maleate in the amount of about 4 w/w % to about 5 w/w %; an animal based palatant in the amount of about 46 w/w % to about 52 w/w %; a non-animal based palatant in the amount of about 11 w/w % to about 14 w/w %; a flavor modifier in the amount of about 0.4 w/w % to about 0.6 w/w %; at least one disintegrant in the amount of about 10 w/w % to about 15 w/w %; at least one binder in the amount of about 5 w/w % to about 7 w/w %; at least one humectant in the amount of 11 w/w % to about 14 w/w %, at least one glidant in the amount of about 1 w/w % to about 3 w/w %, and at least one lubricant in the amount of about 1 w/w % to about 2 w/w %; and wherein each of the w/w % are based on the total weight of the tablet; and wherein the tablet is compressed with a rotary tablet press.

In yet another aspect of the invention, is a palatable soft chewable tablet veterinary composition comprising or containing a therapeutically effective amount of oclacitinib maleate in the amount of about 4 w/w % to about 5 w/w %; an animal based palatant that is pork liver powder in the amount of about 46 w/w % to about 52 w/w %; a non-animal based palatant that is Brewer's yeast in the amount of about 11 w/w % to about 14 w/w %; a flavor modifier that is sodium chloride in the amount of about 0.4 w/w % to about 0.6 w/w %; at least one disintegrant that is a mixture of crospovidone and sodium starch glycolate in the amount of about 10 w/w % to about 15 w/w %; at least one binder that is a mixture of polyethylene glycol 3350 and xanthan gum in the amount of about 5 w/w % to about 7 w/w %; a humectant that is glycerol in the amount of about 11 w/w % to about 14 w/w %; a glidant that is colloidal silicon dioxide in the amount of about 1 w/w % to about 3 w/w %; and at least one lubricant that is a mixture of glycerol monostearate and magnesium stearate in the amount of about 1 w/w % to about 2 w/w %; and wherein each of the w/w % are based on the total weight of the tablet. In yet another aspect of the invention, is a palatable soft chewable tablet veterinary composition containing a therapeutically effective amount of oclacitinib maleate in the amount of about 4 w/w % to about 5 w/w %; an animal based palatant that is pork liver powder in the amount of about 46 w/w % to about 52 w/w %; a non-animal based palatant that is Brewer's yeast in the amount of about 11 w/w % to about 14 w/w %; a flavor modifier that is sodium chloride in the amount of about 0.4 w/w % to about 0.6 w/w %; at least one disintegrant that is a mixture of crospovidone and sodium starch glycolate in the amount of about 10 w/w % to about 15 w/w %; at least one binder that is a mixture of polyethylene glycol 3350 and xanthan gum in the amount of about 5 w/w % to about 7 w/w %; a humectant that is glycerol in the amount of about 11 w/w % to about 14 w/w %; a glidant that is colloidal silicon dioxide in the amount of about 1 w/w % to about 3 w/w %; and at least one lubricant that is a mixture of glycerol monostearate and magnesium stearate in the amount of about 1 w/w % to about 2 w/w %; and wherein each of the w/w % are based on the total weight of the tablet; and wherein the tablet is compressed with a rotary tablet press.

In yet another aspect of the invention, is a palatable soft chewable tablet veterinary composition comprising or containing a therapeutically effective amount of oclacitinib maleate in the amount of about 4 w/w % to about 5 w/w %; an animal based palatant that is pork liver powder in the amount of about 48 w/w % to about 50 w/w %; a non-animal based palatant that is Brewer's yeast in the amount of about 11 w/w % to about 14 w/w %; a flavor modifier that is sodium chloride in the amount of about 0.4 w/w % to about 0.6 w/w %; at least one disintegrant that is a mixture of crospovidone and sodium starch glycolate in the amount of about 10 w/w % to about 15 w/w %; at least one binder that is a mixture of polyethylene glycol 3350 and xanthan gum in the amount of about 5 w/w % to about 7 w/w %; a humectant that is glycerol in the amount of about 11 w/w % to about 14 w/w %; a glidant that is colloidal silicon dioxide in the amount of about 1.5 w/w % to about 2.5 w/w %; and at least one lubricant that is a mixture of glycerol monostearate and magnesium stearate in the amount of about 1 w/w % to about 2 w/w %; and wherein each of the w/w % are based on the total weight of the tablet. In yet another aspect of the invention, is a palatable soft chewable tablet veterinary composition containing a therapeutically effective amount of oclacitinib maleate in the amount of about 4 w/w % to about 5 w/w %; an animal based palatant that is pork liver powder in the amount of about 48 w/w % to about 50 w/w %; a non-animal based palatant that is Brewer's yeast in the amount of about 11 w/w % to about 14 w/w %; a flavor modifier that is sodium chloride in the amount of about 0.4 w/w % to about 0.6 w/w %; at least one disintegrant that is a mixture of crospovidone and sodium starch glycolate in the amount of about 10 w/w % to about 15 w/w %; at least one binder that is a mixture of polyethylene glycol 3350 and xanthan gum in the amount of about 5 w/w % to about 7 w/w %; a humectant that is glycerol in the amount of about 11 w/w % to about 14 w/w %; a glidant that is colloidal silicon dioxide in the amount of about 1.5 w/w % to about 2.5 w/w %; and at least one lubricant that is a mixture of glycerol monostearate and magnesium stearate in the amount of about 1 w/w % to about 2 w/w %; and wherein each of the w/w % are based on the total weight of the tablet; and wherein the tablet is compressed with a rotary tablet press.

In yet another aspect of the invention, is a method of treatment of or prevention of cancer, asthma, atopic dermatitis, autoimmune disorders, pruritus associated with allergic dermatitis, allergies, and chronic respiratory disease in a companion animal; by orally administering the soft chewable tablet composition comprising or containing a therapeutically effective amount of oclacitinib maleate in the amount of about 4 w/w % to about 5 w/w %; an animal based palatant in the amount of about 46 w/w % to about 52 w/w %; a non-animal based palatant in the amount of about 11 w/w % to about 14 w/w %; a flavor modifier in the amount of about 0.4 w/w % to about 0.6 w/w %; at least one disintegrant in the amount of about 10 w/w % to about 15 w/w %; at least one binder in the amount of about 5 w/w % to about 7 w/w %; a humectant in the amount of about 11 w/w % to about 14 w/w %; a glidant in the amount of about 1 w/w % to about 3 w/w %; and at least one lubricant in the amount of about 1 w/w % to about 2 w/w %; and wherein each of the w/w % are based on the total weight of the tablet; and wherein the tablet is compressed with a rotary tablet press.

Preferably, the composition is for the treatment and prevention of atopic dermatitis, pruritus associated with allergic dermatitis and allergies in a companion animal. Preferably, the companion animal is a dog or horse.

In yet another aspect of the invention, is a use of the soft chewable tablet composition comprising or containing a therapeutically effective amount of oclacitinib maleate in the amount of about 4 w/w % to about 5 w/w %; an animal based palatant in the amount of about 46 w/w % to about 52 w/w %; a non-animal based palatant in the amount of about 11 w/w % to about 14 w/w %; a flavor modifier in the amount of about 0.4 w/w % to about 0.6 w/w %; at least one disintegrant in the amount of about 10 w/w % to about 15 w/w %; at least one binder in the amount of about 5 w/w % to about 7 w/w %; a humectant in the amount of about 11 w/w % to about 14 w/w %; a glidant in the amount of about 1 w/w % to about 3 w/w %; at least one lubricant in the amount of about 1 w/w % to about 2 w/w %; and wherein each of the w/w % are based on the total weight of the tablet; and wherein the tablet is compressed with a rotary tablet press; for the treatment of or prevention of cancer, asthma, atopic dermatitis, autoimmune disorders, pruritus associated with allergic dermatitis, allergies, and chronic respiratory disease in a companion animal; by orally administering the soft chewable tablet composition to the companion animal in need thereof. Preferably, the use is for the treatment and prevention of atopic dermatitis, pruritus associated with allergic dermatitis and allergies in a companion animal. The preferred companion animal is a dog or horse.

In yet another aspect of the invention, is the use of the soft chewable composition comprising or containing a therapeutically effective amount of oclacitinib maleate in the amount of about 4 w/w % to about 5 w/w %; an animal based palatant in the amount of about 46 w/w % to about 52 w/w %; a non-animal based palatant in the amount of about 11 w/w % to about 14 w/w %; a flavor modifier in the amount of about 0.4 w/w % to about 0.6 w/w %; at least one disintegrant in the amount of about 10 w/w % to about 15 w/w %; at least one binder in the amount of about 5 w/w % to about 7 w/w %; a humectant in the amount of about 11 w/w % to about 14 w/w %; a glidant in the amount of about 1 w/w % to about 3 w/w %; at least one lubricant in the amount of about 1 w/w % to about 2 w/w %; and wherein each of the w/w % are based on the total weight of the tablet; and wherein the tablet is compressed with a rotary tablet press; for preparing a medicament for the treatment of or prevention of cancer, asthma, atopic dermatitis, autoimmune disorders, pruritus associated with allergic dermatitis, allergies, and chronic respiratory disease in a companion animal. Preferably, for treatment and prevention of atopic dermatitis, pruritus associated with allergic dermatitis and allergies in a companion animal. The preferred companion animal is a dog or horse.

In yet another aspect of the invention, is a soft chewable composition comprising or containing an animal based palatant in the amount of about 45 w/w % to about 55 w/w %; a non-animal based palatant in the amount of about 10 w/w % to about 15 w/w %; a flavor modifier in the amount of about 0.4 w/w % to about 0.6 w/w %; at least one disintegrant in the amount of about 8 w/w % to about 18 w/w %; at least one binder in the amount of about 5 w/w % to about 7 w/w %; a humectant in the amount of about 10 w/w % to about 15 w/w %; a glidant in the amount of about 1 w/w % to about 3 w/w %; at least one lubricant in the amount of about 1 w/w % to about 2 w/w %; and wherein each of the w/w % are based on the total weight of the tablet; for preparing a soft treat for a companion animal; and wherein said treat is compressed with a rotary tablet press.

Definitions

For purposes of the present invention, as described and claimed herein, the following terms and phrases are defined as follows:

"Animal", as used herein, unless otherwise indicated, refers to a vertebrate animal that is non-human, which are members of the taxonomic class Animalia. Non-exclusive examples of animal include companion animals and livestock. Non-exclusive examples of a companion animal include: dog (canine), cat (feline), and horse (equine). Preferred companion animals are dog and cat. More preferred is dog. Non-exclusive examples of livestock include: pig, goat, sheep, and cattle. The term also refers to other animals, for example, deer, ferret, guinea pig, rabbit, zoo animals (e.g., bear, large cats, camel, kangaroo, and the like).

"At least one", as used herein, unless otherwise indicated, refers to one or more agents, e.g., at least one veterinary acceptable excipient means one excipient; it also refers to 2 excipients, 3 excipients, 4 excipients, and the like.

"Composition of the invention", or "composition" as used herein, unless otherwise indicated, refers to a stable, palatable, soft chewable composition intended for oral administration to an animal, preferably a canine animal, a feline animal, or an equine animal.

"Therapeutically effective amount", as used herein, unless otherwise indicated, refers to an amount of an active agent or combination of active agents that treats, prevents, attenuates, ameliorates, delays, or eliminates one or more symptoms in the animal being treated.

"Treatment", "treating", and the like, as used herein, unless otherwise indicated, refers to reversing, alleviating, or inhibiting, for example, pruritus, asthma, allergic dermatitis, and the like. As used herein, these terms also encompass, depending on the condition of the animal, preventing the onset of a disorder or condition, or of symptoms associated with a disorder or condition, including reducing the severity of a disorder or condition or symptoms associated therewith prior to affliction of said condition. Thus, treatment can refer to administration of the composition with at least one veterinary agent to the animal that is not at the time of administration afflicted with said condition. Treating also encompasses preventing the recurrence of symptoms associated therewith.

"Veterinary acceptable" as used herein, unless otherwise indicated, indicates that the substance or composition is compatible chemically and/or toxicologically, with the other ingredients comprising a formulation, composition, and/or the animal being treated therewith.

As used herein, percent of components of the composition refers to percentages of the total weight of the chewable tablet and is referred to as "% w/w" or "w/w %" which defines the mass fraction of the compositional component expressed as a percentage, determined according to the formula $m_i/m_{tot} \times 100$, wherein $m_i$ is the mass of the substance of interest present in the composition, and $m_{tot}$ is the total mass of the composition. The w/w % also define the amount of an active ingredient or other compositional component in a granulation mixture, e.g., amount of palatant in the chewable granulation.

DETAILED DESCRIPTION

The present invention provides a stable, palatable, soft chewable composition for oral administration of a therapeutically effective amount of a veterinary acceptable active agent, and wherein said chewable tablet is compressed on a rotary compression tablet press.

A tablet press is a mechanical device that compresses powder (i.e., granulations and or blends) into tablets of uniform size and weight. To form a tablet, the granulated material must be metered into a cavity formed by two punches and a die, and then the punches must be pressed together with great force to fuse the material together. A tablet is formed by the combined pressing action of two punches and a die. In the first step of a typical operation, the bottom punch is lowered in the die creating a cavity into which the granulated feedstock is fed. The exact depth of the lower punch can be precisely controlled to meter the amount of powder that fills the cavity. The excess is scraped from the top of the die, and the lower punch is drawn down and temporarily covered to prevent spillage. Then, the upper punch is brought down into contact with the powder as the cover is removed. The force of compression is delivered by high pressure compression rolls which fuse the granulated material together into a hardened tablet. After compression, the lower punch is raised to eject the tablet.

There are 2 types of tablet presses: single-punch and rotary tablet presses. Most high-speed tablet presses take the form of a rotating turret that holds any number of punches. As they rotate around the turret, the punches come into contact with cams which control the punch's vertical position. Punches and dies are usually custom made for each application, and can be made in a wide variety of sizes, shapes, and can be customized with manufacturer codes and scoring lines. Depending on tablet size, shape, material, and press configuration, a typical modern press can produce from 250,000 to over 1,000,000 tablets an hour. Common manufacturers of tablet presses include Natoli, Stokes, Fette Compacting, Korsch, Kikusui, Manesty, B&D, PTK, IMA and Courtoy.

Soft chewable tablets have typically been manufactured by blending and extrusion, blending and knock-out, and use of injection molds, using waxy, oily, doughs. For extrusion, pre-mixed ingredients are introduced into an extruder barrel with a single or twin screw therein, then mixed, coagulated, expanded and sheared into a blended mixture, followed by application of additional heat or water for proper extrusion. The blended and extruded mixture is then formed into a desired shape on a die plate and cut into individual units. Texture, shape and weights of the chews from batch to batch of extruded material can be inconsistent and tend to lack efficiency.

Rotary molding machines (e.g., Formax F6™ by the Formax Corporation) work by displacing dough between a rotary mold roller and removal from the mold without a punch mechanism. Injection molding consists of high pressure, and potentially high temperature, injection of the raw material into a mold which shapes the material into any desired shape. It is most typically used in mass-production processes where the same part is being created thousands or even millions of times in succession. Molds can be of a single cavity or multiple cavities. In multiple cavity molds, each cavity can be identical and form the same parts or can be unique and form multiple different geometries during a single cycle. Generally, the final product must be displaced from the mold. The use of extruders, forming machines and rotary molding machines exhibit problems associated with the weight and physical forms of a final dosage form. Moreover, the use of such technologies may require conditioning of the final dosage form (e.g. drying or curing final formed structure) for consolidation of shape and structure of formed structure. Use of such technologies, equipment and processes is complex, cumbersome, and something that is not traditionally used in a typical pharmaceutical oral solid dosage form manufacturing set-up.

As described herein, the stable, palatable, soft chew tablet is compressed with a standard rotary tablet compression machine.

According to the invention, a preferred veterinary acceptable active agent is oclacitinib, or a veterinary acceptable salt thereof. Oclacitinib is the compound of Formula 1,

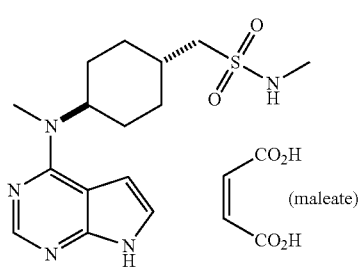

(1)

(maleate)

and has the chemical name: N-methyl-1-{trans-4-[methyl (7H-pyrrolo[2,3-d]pyrimidin-4-yl)amino] cyclohexyl}methanesulfonamide. The compound of Formula (1) and it's commercial salt, maleate, is referred to herein as Apoquel®; depicted above.

Additional veterinary acceptable salts of oclacitinib include, but are not limited to: acetate, ascorbate, aspartate, benzoate, besylate, bicarbonate/carbonate, bisulphate/sulphate, borate, camsylate, citrate, edisylate, ketoglutarate, esylate, formate, fumarate, gluceptate, gluconate, glucuronate, glycerophosphate, hexafluorophosphate, hibenzate, hydrochloride/chloride, hydrobromide/bromide, hydroiodide/iodide, isethionate, lactate, malate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Apoquel is a Janus Kinase inhibitor (JAK-i) with efficacy against Janus Kinase-1 (JAK-1), Janus Kinase-2 (JAK-2) and Janus Kinase-3 (JAK-3), and particularly, JAK-1. Accordingly, it is useful as a therapeutic agent for cancer, asthma, atopic dermatitis, autoimmune disorders, control of pruritus, allergies, chronic respiratory disease and other indications where immunosuppression and/or immuno-modulation would be desirable. A preferred use is for the control of pruritus associated with allergic dermatitis and control of atopic dermatitis in companion animals, particularly dogs.

Accordingly, the compound of Formula 1 or its veterinary acceptable salts and veterinary compositions can be used to treat a variety of conditions or diseases such as:

asthma and other obstructive airways diseases, including chronic or inveterate asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease;

autoimmune diseases or disorders, including those designated as single organ or single cell-type autoimmune disorders, for example autoimmune hemolytic anemia, autoimmune atrophic gastritis of pernicious anemia, autoimmune encephalomyelitis, autoimmune orchitis, autoimmune thrombocytopenia, sympathetic ophthalmia, ulcerative colitis and membranous glomerulopathy, those designated as involving systemic autoimmune disorder, for example systemic lupus erythematosis, systemic sclerosis, and bullous pemphigoid, osteoarthritis (i.e., degenerative joint disease), non-erosive immune-mediated polyarthritis, traumatic arthritis, and additional autoimmune diseases, which can be O-cell (humoral) based or T-cell based, including autoimmune alopecia and thyroiditis;

cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, and angiogenic-associated disorders including solid tumors;

eye diseases, disorders or conditions including autoimmune diseases of the eye, keratoconjunctivitis and keratoconjunctivitis sicca (dry eye);

intestinal inflammations, allergies or conditions including ulcerative colitis, inflammatory bowel disease, coeliac diseases, proctitis, eosinophilic gastroenteritis, and mastocytosis;

skin diseases, conditions or disorders including atopic dermatitis, eczema, psoriasis, scleroderma, pruritus and other pruritic conditions;

allergic reactions including allergic dermatitis in an animal including horse allergic diseases such as bite hypersensitivity, summer eczema and sweet itch.

The Formula 1 compound may be administered in a veterinary acceptable form (e.g., soft chew tablet) either alone or in combination with one or more additional agents that modulate an animal's immune system or with anti-inflammatory agents. These agents may include but are not limited to cyclosporin A, rapamycin, FK-506 (tacrolimus), leflunomide, deoxyspergualin, mycophenolate, azathioprine, daclizumab, aspirin, acetaminophen, ibuprofen, naproxen, piroxicam, and anti-inflammatory steroids (e.g. prednisolone or dexamethasone). These agents may be administered as part of the same or separate dosage forms, via the same or different routes of administration, and on the same or different administration schedules according to standard veterinary practice known to one skilled in the art.

According to the invention, other veterinary active JAK inhibitor agents that can be formulated into the palatable soft chew composition besides Apoquel®, include: 3-(3-((2-methyl-7H-pyrrolo[2,3-d]pyrimidin-4-yl)amino)piperidin-1-yl)-3-oxopropanenitrile and 1-((3R,4S)-4-cyanotetrahydro-2H-pyran-3-yl)-3-((2-fluoro-6-methoxypyridin-4-yl)amino)-1H-pyrazole-4-carboxamide. In addition to the JAK inhibitor agents, the following non-limiting veterinary active agents can be formulated with the palatable soft chew composition of the invention, and include: antimicrobials/antibacterials (e.g., quinolones, fluoroquinolones, cephalosporins (1st, 2nd, 3rd, and 4th generation), tetracyclines, penicillins, β-lactams, macrolides, phenicols, pyrantel pamoate (embonate), carbapenems, and the like); antiparasitics including isoxazole analogs (e.g., (S)-1-(5'-(5-(3,5-dichloro-4-fluorophenyl)-5-(trifluoromethyl)-4,5-dihydroisoxazol-3-yl)-3'H-spiro[azetidine-3,1'-isobenzofuran]-1-yl)-2-(methylsulfonyl)ethan-1-one (sarolaner); 4-(5-(3-chloro-5-(trifluoromethyl)phenyl)-5-(trifluoromethyl)-4,5-dihydroisoxazol-3-yl)-N-(2-oxo-2-((2,2,2-trifluoroethyl)amino)ethyl)-1-naphthamide (afoxolaner); 4-(5-(3,5-dichlorophenyl)-5-(trifluoromethyl)-4,5-dihydroisoxazol-3-yl)-2-methyl-N-(2-oxo-2-((2,2,2-trifluoroethyl)amino)ethyl)-benzamide (fluralaner); and 3-methyl-N-{2-oxo-2-[(2,2,2-trifluoroethyl)amino]ethyl}-5-[(5S)-5-(3,4,5-trichlorophenyl)-5-(trifluoromethyl)-4,5-dihydro-1,2-oxazol-3-yl]thiophene-2-carboxamide (lotilaner)); macrocyclic lactones and milbemycins (e.g., doramectin, eprinomectin, ivermectin, moxidectin, milbemycin oxime, and the like); antiprotozoals (e.g., metronidazole, doxycycline, amprolium, atovaquone, benzonidazol, and the like); anti-fungals (e.g., ketoconazole, fluconazole, and the like); inotropes (e.g., pimobendan); neurologic agents (e.g., gabapentin, pregabalin, diazepam, phenobarbital, and the like); cardiovascular agents (e.g., ACE-inhibitors (e.g., benazepril, lisinopril, accupril, ramipril, and the like), beta-blockers (e.g., nadolol, metoprolol, atenolol, propranolol, and the like), and 5HT2B inhibitors); NSAIDs and other analgesics (carprofen, ketoprofen, deracoxib, flunixin, nimesulide, firocoxib, mavacoxib, robenacoxib, meloxicam, tramadol, amantadine, dexamethasone, and the like); thyroid agents (e.g., levothyroxine, methimazole, and the like); steroids (e.g., prednisone, prednisolone, dexamethasone, and the like); and behavior-modifying agents and sedatives (e.g., diazepam, xylazine, alprazolam, acepromazine, detomidine, amitriptyline, clomipramine, midazolam, and the like).

In a preferred aspect of the invention, the composition comprises or contains the active veterinary agent: oclacitinib maleate (Apoquel®) in an amount of about 4 w/w % to about 5 w/w % of the total weight of the tablet. The preferred amount of the active agent, oclacitinib maleate is about 4 w/w % (e.g., 4.03 w/w %).

The composition of the invention comprises or contains at least one animal based palatant and one non-animal based palatant. The palatants are in an amount of about 55 w/w % to about 70 w/w % of the total tablet weight. Palatants are used to alter or enhance the flavor(s) of natural food products such as meats and vegetables, or creating additional flavor for food products that do not have the desired flavors such as snacks and oral medications. Most types of palatants are focused on scent and taste. Artificial palatants are chemically synthesized compounds that are used to flavor food items and are often formulated with the same chemical compounds found in natural palatants. Most artificial flavors are specific and often complex mixtures of singular naturally occurring flavor compounds to either imitate or enhance a natural flavor. These mixtures are formulated by flavorists to give a food product a unique flavor and to maintain flavor consistency between different product batches or after recipe changes. The list of known flavoring agents includes thousands of molecular compounds, and can be combined to achieve flavors like chicken, turkey, beef, pork, lamb, fish, egg, cheese, seafood, smoke, and many others. A natural palatant is defined as the essential oil, oleoresin, essence or extract, protein hydrolysate, distillate, or any product of roasting, heating or enzymolysis, which contains the flavoring constituents derived from a spice, fruit or fruit juice, vegetable or vegetable juice, edible yeast (active and inactive), herb, bark, bud, root, leaf or any other edible portions of a plant, meat, seafood, poultry, eggs, dairy products, or fermentation products thereof; and can include sweeteners like sucrose; whose primary function in food is flavoring rather than nutritional. Natural palatants include chicken, turkey, beef, pork, lamb, fish, egg, cheese, seafood, vegetable and vegetable matter, yeast (e.g., brewer's yeast) and mixtures thereof. Yeast extracts are also included in the natural flavors. Flavor (taste) modifiers, for example sodium chloride, potassium chloride, are also construed herein as a palatant. Natural meat palatants can be obtained from meat, meat products, organ meat, yeast extracts, vegetable matter, and mixtures thereof. For example, an oral veterinary composition medication might include animal product-based flavorings such as dried or powdered meat and meat parts such as beef, pork, chicken, turkey, fish, and lamb; organ meats such as liver and kidney; meat meals, bone meals and ground bone; and animal-derived food such as casein, milk (which may include dry forms and lowered fat forms, such as dry skim milk), yogurt, gelatin, cheese and egg (collectively, "animal origin flavorings") may be utilized. The natural products may or may not be sterilized by heat or other types of radiation, e.g., gamma-radiation. The preferred palatant for the stable, palatable, chewable composition is a natural animal based palatant. The composition of the invention comprises or contains at least two palatants in the amount of about 55 w/w % to about 70 w/w % of the total weight of the chewable tablet. The composition comprises or contains at least one animal based palatant in the amount of about 45 w/w % to about 55 w/w % of the total weight of the tablet. The preferred animal based palatant is in the amount of about 46 w/w % to about 52 w/w % of the total weight of the tablet. The preferred animal based palatant is in the amount of about 48 w/w % to 50 w/w % of the total weight of the tablet. The preferred animal based palatant is derived from organ meat. The preferred organ meat is derived from pork liver. The preferred animal based palatant is pork liver powder. The composition comprises or contains about 10 w/w % to about 15 w/w % of the total weight of the tablet of a non-animal based palatant; and preferably about 11 w/w/% to about 14 w/w % of the total weight of the tablet. Preferably, the non-animal based palatant is yeast. The preferred yeast is Brewer's yeast. The composition also comprises or contains about 0.4 w/w % to about 0.6 w/w % of the total weight of the tablet of a flavor modifier. The preferred flavor modifier is sodium chloride. The composition comprises or contains about 48 w/w % to about 50 w/w % of the total weight of the tablet of an animal based palatant; about 11 w/w % to about 14 w/w % of a non-animal based palatant, and wherein the w/w % are based on the total weight of the tablet.

The stable, palatable chewable composition comprises or contains at least one veterinary acceptable excipient. The veterinary acceptable excipient includes excipients that are construed as binders, disintegrants, lubricants, glidants, humectants, antioxidants, and colorants. The soft chew tablet comprises or contains the active agent, oclacitinib maleate, an animal based palatant, a non-animal based palatant, a flavor modifier, and at least one each of a binder, disintegrant, humectant, lubricant, and glidant; and is compressed using a rotary tablet press.

Binders are used to add cohesiveness to the composition, thereby providing the necessary bonding to form a cohesive mass and to ensure a suitable compacted tablet form. These binding agents are conventionally used in direct compression tablets and are described in Lieberman et. al., Veterinary Dosage Forms, 2 Ed., Vol. 1, (1990). Non-limiting examples of veterinary acceptable binders include, but are not limited to: microcrystalline cellulose, carboxymethyl cellulose, sodium carboxy methyl cellulose, hydroxypropyl cellulose, polyvinylpyrrolidone (e.g., povidone (Kollidon 25, 30, and 90) and co-povidone (Kollidon VA 64), polyethylene glycol (PEG), acacia, corn syrup solids, tragacanth gum, xanthan gum, gelatin, carnauba wax, alginate, and mixtures thereof. Polyethylene glycol (PEG) is a polyether compound with many applications, from industrial manufacturing to medicine. PEG is also known as polyethylene oxide (PEO) or polyoxyethylene (POE), depending on its molecular weight. The structure of PEG is commonly expressed as $H(OCH_2CH_2)_nOH$, where n is an integer ≥3. PEG's are prepared by polymerization of ethylene oxide and are commercially available over a wide range of molecular weights from 300 g/mol to 10,000,000 g/mol. PEG's are commercially available. A PEG with an n of 9 has an average weight of about 400 daltons (g/mole) and is conveniently labeled as PEG 400. Similarly, a PEG with an n of 45 has an average weight of about 2000 daltons and is conveniently labeled as PEG 2000. PEG 3350 is a PEG with a molecular weight of 3350 g/mol. It is commonly used in the pharmaceutical and veterinary industry. The composition of the invention comprises or contains about 5 w/w % to about 7 w/w % of the total weight of the tablet of at least one binder. The preferred binding agent for the composition of the invention is PEG 3350. The composition further comprises or contains at least one binder that is a gum selected from the group consisting of tragacanth gum, xanthan gum, arabic gum, cellulose gum, guar gum, locust bean gum, or a mixture thereof; and preferably xanthan gum, in the amount of about 0.3 w/w % to about 0.7 w/w % of the total weight of the tablet, preferably, about 0.4 w/w % to about 0.6 w/w % of the total weight of the tablet, and more preferably about 0.5 w/w % of the total weight of the tablet. The composition comprises or contains about 5 w/w % to about 6 w/w % of the total weight of the tablet of PEG 3350.

The stable, palatable composition comprises or contains at least one veterinary acceptable excipient that is a disintegrant, thereby providing a means for the dosage form to expand and dissolve more readily when wet and/or break apart while being chewed. Disintegrants are conventionally used in direct compression tablets and are described in Lieberman et al., Veterinary Dosage Forms, 2 Ed., Vol. 1, (1990). Non-exclusive examples of veterinary acceptable disintegrants include: starch including pregelatinized and modified starches, microcrystalline cellulose, methyl cellulose, carboxymethyl cellulose, carboxymethyl cellulose sodium, crospovidone, magnesium aluminum silicate, guar gum, alginic acid, sodium alginate, calcium alginate, chitosan, croscarmellose sodium (e.g., Ac-Di-Sol®), sodium starch glycolate, and the like, and mixtures thereof. Preferred disintegrant(s) are selected from the group consisting of starch, carboxymethyl cellulose sodium, crospovidone, croscarmellose sodium, and sodium starch glycolate, and mixtures thereof. The more preferred disintegrants are sodium starch glycolate and crospovidone, or a mixture thereof. The most preferred disintegrant is a mixture of crospovidone and sodium starch glycolate. The amount of disintegrant(s) in the composition is about 8 w/w % to about 18 w/w % of the total weight of the tablet. The preferred amount of disintegrant(s) in the composition is about 10 w/w % to about 15 w/w % of the total weight of the tablet. The composition comprises or contains about 4 w/w % to about 9 w/w % of the total weight of the tablet of crospovidone and about 4 w/w % to about 9 w/w % of the total weight of the tablet of sodium starch glycolate.

The stable, palatable composition comprises or contains at least one veterinary acceptable excipient that is a humectant. Humectants are considered hygroscopic in that they impart moisture to the composition. Non-limiting examples of humectants for the composition include, but are not limited to: glycerin (glycerol), hyaluronic acid, sorbitol, urea, alpha hydroxy acids, sugars, lactic acid, propylene glycol, glyceryl triacetate, lithium chloride, polyols like sorbitol, xylitol and maltitol, polymeric polyols like polydextrose, natural extracts like quillaia, hexadecyl, myristyl, isodecyl and isopropyl esters of adipic, lactic, oleic, stearic, isostearic, myristic and linoleic acids, as well as many of their corresponding alcohol esters (e.g. sodium isostearyl-2-lactylate, sodium caproyl lactylate). The preferred humectant is glycerol and is in the amount of about 10 w/w % to about 15 w/w % of the total weight of the tablet. The preferred amount of humectant is about 11 w/w % to about 14 w/w % of the total weight of the tablet.

The stable, palatable composition comprises or contains at least one veterinary acceptable excipient that is a lubricant. Lubricants are used to enhance product flow by reducing inter-particulate friction and to prevent compositional ingredients from clumping together and from sticking to the tablet punches. Lubricants also ensure that tablet formation and ejection can occur with low friction between the tablet and die wall. Non-limiting examples of lubricants include: talc, magnesium stearate, glyceryl monostearate, boric acid, sodium benzoate, sodium olete, sodium acetate, sodium lauryl sulfate, magnesium lauryl sulfate, and mixtures thereof. Preferred lubricants include talc, magnesium stearate, and glyceryl monostearate. The more preferred lubricants are magnesium stearate, glycerol monostearate, and mixtures thereof. The composition comprises glycerol monostearate and magnesium stearate as lubricants in the amount of about 1 w/w % to about 2 w/w % of the total weight of the tablet.

The stable, palatable composition comprises or contains at least one veterinary acceptable excipient that is a glidant. Glidants are used to promote powder flow by reducing interparticle friction and cohesion. These are used in combination with lubricants as they have no ability to reduce die wall friction. Examples include fumed silica, colloidal silicon dioxide, talc, and magnesium carbonate. The preferred glidant is colloidal silicon dioxide and is in the amount of about 1 w/w % to about 3 w/w % of the total weight of the tablet. The preferred amount of glidant in the composition is about 1.5 w/w % to about 2.5 w/w % of the total weight of the tablet.

The stable, palatable composition can further comprise or contain at least one veterinary acceptable excipient that is an antioxidant. Non-exclusive examples of antioxidants include: ascorbic acid, vitamin E (tocopherol), vitamin E derivatives, sodium metabisulphite, ascorbyl palmitate, fumaric acid, citric acid, malic acid, sodium ascorbate, butylated hydroxyanisole (BHA), and butylated hydroxytoluene (BHT), propyl gallate, thioglycerol, and the like, and mixtures thereof. Preferred antioxidants include BHA, BHT, citric acid, and propyl gallate, and mixtures thereof. The amount of antioxidant(s) in the composition can range from about 0 w/w % to about 0.05 w/w % of the total weight of the tablet.

The stable, palatable composition can also comprise or contain at least one veterinary acceptable excipient that is a colorant. Colorants can be added to the composition to enhance its physical appearance and can be in the amount of about 1 w/w % (or less) of the total weight of the tablet.

The stable, palatable composition is prepared as a common blend that can be tableted into different tablet sizes with the same w/w % values of active agent, palatants, and excipients that can be manufactured by general granulation, blending, milling, sieving, compression, and packaging procedures.

The composition of the invention can be prepared by known procedures for manufacturing common blends and tableting via rotary compression.

A binder solution is prepared by melting and mixing the binder, PEG 3350, with a lubricant (glyceryl monostearate) and glycerol at a temperature of about 90-100° C. to prepare binder solution (A). Alternatively, a second binder solution can be prepared containing solubilized xanthan gum in glycerol to prepare binder solution (B). The active-flavored dry-blended granulation is prepared by mixing (blending) and granulating the active agent (e.g., oclacitinib maleate) with a palatant, disintegrants, a binder (xanthan gum), flavor modifier, and glidant in a high shear granulator. The dry blend is milled and then mixed with binder solution (A) to prepare a wet granulation. Alternatively, the active-flavored dry-blended granulation is first mixed with a portion of glycerol prior to addition and further mixing with binder solution (A) to prepare the wet granulation. In addition, the active-flavored dry-blended granulation (without binder) can be mixed with binder solutions (A) and (B) to prepare the wet granulation. The wet granulation is milled and then cured for about 1 to 3 hours at about 45° C. to 65° C. in a fluid bed dryer. An extra-granular composition comprising a glidant, a palatant, and disintegrant was prepared by blending the components together and then milled. The cured active-flavored granulation and extra-granular composition were blended together in a low-shear bin-type blender and a lubricant is sifted into the blend. The final blend is then compressed using a rotary tablet press. The final tablets were packaged in HDPE bottles and/or blisters.

The finished tablets comprise about 4.03 w/w % of the total weight of the tablet of oclacitinib maleate. Depending upon tablet size, preferred tablet strengths are 3.6 mg, 5.4 mg, and 16.0 mg oclacitinib per tablet. Further, tablets can be prepared to have anywhere from 1, 2, 3, 4, 5, 6, 7, 8, 9, 10, 11, 12, 13, 14, 15, 16, 7, 18, 19, 20, 21, 22, 23, 24, 25 mg, and the like, of oclacitinib, including additional fractional amounts, e.g., 2.5, 7.7, 12.3, 16.6, 22.3, and the like, by altering the size of the tablet die during compression since this composition is a common blend.

The therapeutically effective dose of oclacitinib in dogs is 0.4 to 0.6 mg/kg body weight, administered orally, twice daily for up to 14 days, and then administered once daily for maintenance therapy. Depending upon the weight of the dog, single chewable tablets can be administered, or multiple tablets can be administered to ensure the effective mg/kg dose amount is administered for larger breed dogs. In addition, appropriate dose amounts can be administered to cats, horses, and other animals; these doses may be different and could range from 0.1 to 1 mg/kg body weight depending on the animal and half-life pharmacokinetics of oclacitinib in the non-canine animals.

Average tablet in-process results from the common-blend apoquel chewable composition is shown in Table 1.

TABLE 1

Tablet In-Process Results from the Apoquel Common Blend

| Process Parameter | Tablet Strength | | |
|---|---|---|---|
| | 3.6 mg | 5.4 mg | 16 mg |
| Weight Uniformity (mg) | 119 | 182 | 534 |
| Tablet Thickness (mm) | 3.78 | 4.40 | 5.87 |
| Tablet Hardness (kp) | 2.0 | 3.3 | 5.8 |
| Disintegration Time (sec) | 150 | 190 | 252 |
| Friability^ | 0.237 | 0.014 | 0.013 |

^(% w/w at 100 rotation)

COMPOSITIONAL EXAMPLES

The invention is further described by the following examples which further illustrate the invention, and is not intended, nor should it be interpreted to, limit the scope of the invention.

Example 1. Tablet Composition 1

| Example 1. Tablet Composition 1 | |
|---|---|
| Excipient/Active | w/w % of Total Tablet |
| Oclacitinib maleate | 4.03 |
| Animal based palatant | 48.64 |
| Non-animal based palatant | 13.13 |
| Disintegrants | 11.40 |
| Glidant | 2.11 |
| Lubricants | 1.34 |
| Binders | 6.07 |
| Humectant | 12.72 |
| Flavor modifier | 0.56 |
| Total | 100 |

Example 2. Tablet Composition 2

| Example 2. Tablet Composition 2 | |
|---|---|
| Excipient/Active | w/w % of Total Tablet |
| Oclacitinib maleate | 4.03 |
| Animal based palatant | 48.64 |
| Non-animal based palatant | 11.63 |
| Disintegrants | 12.90 |
| Glidant | 2.11 |
| Lubricants | 1.34 |
| Binders | 6.07 |
| Humectant | 12.72 |
| Flavor modifier | 0.56 |
| Total | 100 |

Example 3. Tablet Composition 3

| Example 3. Tablet Composition 3 | |
| --- | --- |
| Excipient/Active | w/w % of Total Tablet |
| Oclacitinib maleate | 4.03 |
| Anir al based palatant | 48.64 |
| Non-animal based palatant | 13.63 |
| Disintegrants | 11.4 |
| Glidant | 1.61 |
| Lubricants | 1.34 |
| Binders | 6.07 |
| Humectant | 12.72 |
| Flavor modifier | 0.56 |
| Total | 100 |

Example 4. Tablet Composition 4

| Example 4. Tablet Composition 4 | |
| --- | --- |
| Excipient/Active | w/w % of Total Tablet |
| Oclacitinib maleate | 4.03 |
| Animal based palatant | 46.2 |
| Non-animal based palatant | 12.5 |
| Disintegrants | 13.4 |
| Glidant | 1.85 |
| Lubricants | 1.70 |
| Binders | 6.4 |
| Humectant | 13.5 |
| Flavor modifier | 0.42 |
| Total | 100 |

Example 5. Tablet Composition 5

| Example 5. Tablet Composition 5 | |
| --- | --- |
| Excipient/Active | w/w % of Total Tablet |
| Oclacitinib maleate | 4.03 |
| Animal based palatant | 48.1 |
| Non-animal based palatant | 13.8 |
| Disintegrants | 13.9 |
| Glidant | 1.55 |
| Lubricants | 1.04 |
| Binders | 5.2 |
| Humectant | 11.8 |
| Flavor modifier | 0.58 |
| Total | 100 |

Biological

Palatable soft chew compositions containing oclacitinib maleate were prepared and evaluated for palatability and stability.

Palatability

To assess palatability, mature 3-9 year old beagle dogs (N=48) were randomly assigned to a 2-sequence, 2-period crossover design study. Animals were offered a placebo (T01) soft chew tablet or a test soft chew tablet containing 5.4 mg of Apoquel® (T02-composition 1). One tablet was offered for free oral consumption daily for three consecutive days for each group of dogs (N=24/group). Acceptability for the placebo (T01) and the Apoquel® (T02) soft chew tablets was 79.9% and 78.5%, respectively.

In another palatability study, mixed breed dogs (N=96) that were >1-year old were randomly assigned to a 4-period crossover design study. Animals were offered placebo (T01) soft chew tablet or a test soft chew tablet containing 5.4 mg of Apoquel® [T02-composition 1; T03-composition 2; and T04-composition 3]. One tablet was offered for free oral consumption daily for three consecutive days for each group of dogs (N=24/group). Acceptability for the placebo and the Apoquel® soft chew tablets was 85% (T01), 84% (T02), 83% (T03), and 83% (T04). Overall, the compositions containing oclacitinib were palatable.

Stability

The soft chew tablets were shown to be stable at 1 and 2 months at 40° C./75% relative humidity in HDPE bottles for the 3.6 mg, 5.4 mg, and 16 mg soft chew tablets with assay (% of label claim) results ranging from 98.3 to 101.5%.

We claim:

1. A palatable soft chewable tablet veterinary composition comprising:
    a) therapeutically effective amount of oclacitinib or a veterinary acceptable salt thereof;
    b) an animal based palatant that is pork liver powder in the amount of about 45 w/w % to about 55 w/w %;
    c) a non-animal based palatant that is Brewer's yeast in the amount of 10 w/w % to 15 w/w % and the humectant glycerol in the amount of 10 w/w % to 15 w/w %;
    d) a veterinary acceptable excipient selected from at least one each of a disintegrant in the amount of 10 w/w % to 15 w/w %, a binder in the amount of 5 w/w % to 7 w/w %, a lubricant in the amount of 1 w/w % to 2 w/w %, a glidant in the mount of 1 w/w % to 3 w/w % and flavor modifier; and wherein the w/w % is the weight percent of the total weight of the tablet; and wherein the soft-chewable tablet is compressed with a rotary tablet press.

2. The composition of claim 1, wherein the veterinary acceptable salt of oclacitinib is the maleate salt.

3. The composition of claim 2, wherein the veterinary acceptable disintegrant is a mixture of crospovidone and sodium starch glycolate.

4. The composition of claim 2, wherein the veterinary acceptable binder comprises a mixture of polyethylene glycol and a gum.

5. The composition of claim 4, wherein the polyethylene glycol is polyethylene glycol 3350 and the gum is xanthan gum.

6. The composition of claim 5 wherein the veterinary acceptable glidant is colloidal silicon dioxide and the flavor modifier is sodium chloride in the amount of 0.4 w/w % to 0.6 w/w %.

7. The composition of claim 6, wherein the veterinary acceptable lubricant is a mixture of magnesium stearate and glycerol monostearate.

8. A palatable soft chewable tablet veterinary composition comprising:
    a) a therapeutically effective amount of oclacitinib maleate in the amount of 4 w/w % to 5 w/w %;
    b) an animal based palatant that is pork liver powder in the amount of 46 w/w % to 52 w/w %;
    c) a non-animal based palatant that is Brewer's yeast in the amount of 11 w/w % to 14 w/w % and the humectant, glycerol, in the amount of 11 w/w % to 14 w/w %;

d) a disintegrant that is a mixture of crospovidone and sodium starch glycolate in the amount of 10 w/w % to 15 w/w %, a binder that is a mixture of polyethylene glycol and a gum in the amount of 5 w/w % to 7 w/w %, a lubricant that is a mixture of magnesium stearate and glycerol monostearate in the amount of 1 w/w % to 2 w/w %, a glidant in the amount of 1 w/w % to 3 w/w % and the flavor modifier sodium chloride in the amount of 0.4 w/w % to 0.6 w/w %; and wherein the w/w % is the weight percent of the total weight of the tablet; and wherein the soft chewable tablet is compressed with a rotary tablet press.

9. The composition of claim 8, wherein the polyethylene glycol is polyethylene glycol 3350 and the gum is xanthan gum.

10. A method of treating atopic dermatitis or pruritis associated with allergic dermatitis and allergies in a companion animal by administering a palatable soft chewable tablet veterinary composition comprising:
   a) a therapeutically effective amount of oclacitinib, or a veterinary acceptable salt thereof;
   b) an animal based palatant that is pork liver powder in the amount of 45 w/w % to 55 w/w %, a non-animal based palatant that is Brewer's yeast in the amount of 10 w/w % to 15 w/w %, the humectant glycerol in the amount of 10 w/w % to 15 w/w %, and a flavor modifier;
   c) a disintegrant that is a mixture of crospovidone and sodium starch glycolate in the amount of 10 w/w % to 15 w/w %, a binder that is a mixture of polyethylene glycol and a gum in the amount of 5 w/w % to 7 w/w %, a lubricant that is a mixture of magnesium stearate and glycerol monostearate in the amount of 1 w/w % to 2 w/w %, a flavor modifier in the amount of 0.4 w/w % to 0.6 w/w %, and a glidant in the amount of 1 w/w % to 3 w/w %; and wherein the w/w % is the weight percent of the total weight of the tablet, and wherein the soft chewable tablet is compressed on a rotary tablet press.

11. The method of claim 10, wherein the companion animal is a dog.

12. The method of claim 10, wherein the veterinary acceptable salt of oclacitinib is the maleate salt the polyethylene glycol is polyethylene glycol 3350 and the gum is xanthan gum.

13. The method of claim 12, wherein the therapeutic amount of oclacitinib maleate is 4 w/w % to 5 w/w %.

14. The method of claim 13, wherein the amount of pork liver powder is in the amount of 46 w/w % to 52 w/w % and the amount of Brewer's yeast is in the of 11 w/w % to 14 w/w %.

15. The method of claim 14, wherein the the flavor modifier is sodium chloride and the glidant is colloidal silicon dioxide.

* * * * *